(12) United States Patent
Muser

(10) Patent No.: US 12,251,117 B2
(45) Date of Patent: Mar. 18, 2025

(54) DRILL GUIDE ASSEMBLY

(71) Applicant: Conmed Corporation, Largo, FL (US)

(72) Inventor: Andrew Muser, St. Pete Beach, FL (US)

(*) Notice: Subject to any disclaimer, the term of this patent is extended or adjusted under 35 U.S.C. 154(b) by 84 days.

(21) Appl. No.: 17/688,017

(22) Filed: Mar. 7, 2022

(65) Prior Publication Data
US 2022/0183702 A1   Jun. 16, 2022

Related U.S. Application Data

(62) Division of application No. 16/260,689, filed on Jan. 29, 2019, now Pat. No. 11,266,422.

(60) Provisional application No. 62/728,946, filed on Sep. 10, 2018, provisional application No. 62/623,643, filed on Jan. 30, 2018.

(51) Int. Cl.
*A61B 17/17* (2006.01)
*A61B 17/00* (2006.01)
*A61B 90/00* (2016.01)

(52) U.S. Cl.
CPC .......... *A61B 17/17* (2013.01); *A61B 17/1714* (2013.01); *A61B 17/1764* (2013.01); *A61B 2017/00407* (2013.01); *A61B 2090/062* (2016.02)

(58) Field of Classification Search
CPC ................ A61B 17/16; A61B 17/1633; A61B 5/150534; A61B 5/150603; A61B 5/150633; A61B 5/150664; A61B 17/8875; A61B 17/8894; A61B 17/8897; A61B 17/32; A61B 17/1746; A61B 90/11
See application file for complete search history.

(56) References Cited

U.S. PATENT DOCUMENTS

| | | | | |
|---|---|---|---|---|
| 3,336,822 A | * | 8/1967 | Armacost | B23B 49/023 408/241 R |
| 3,535,956 A | * | 10/1970 | Gnoth | B23B 49/023 408/87 |
| 4,708,139 A | * | 11/1987 | Dunbar, IV | A61B 17/1764 D24/140 |
| 5,236,289 A | * | 8/1993 | Salyer | B25B 15/008 408/127 |

(Continued)

FOREIGN PATENT DOCUMENTS

| | | | | |
|---|---|---|---|---|
| EP | 0613658 A1 | * | 7/1994 | ............ A61B 17/16 |
| WO | WO-2017067768 A1 | * | 4/2017 | ............ A61B 17/17 |

*Primary Examiner* — Anu Ramana
(74) *Attorney, Agent, or Firm* — Bond, Schoeneck & King, PLLC; Frederick J. M. Price

(57) ABSTRACT

A drill guide assembly for accurate and stable drilling of a bone tunnel. The drill guide assembly includes a guide body having first and second ends, and a slot extending from the first end toward the second end. The drill guide assembly also includes a curved guide arm having a first arm connected at an angle to a second arm. The first arm terminates in a distal tip. The second arm has first and second sides, and is slidable within the slot of the guide body. The second arm also includes detents along its second side. A locking mechanism is attached at the first end of the guide body and in a first position, and the locking mechanism is engaged with one of the detents. The drill guide assembly also includes a clamp mechanism attached at the second end of the guide body and a guide sleeve removably extending therethrough.

2 Claims, 15 Drawing Sheets

(56) References Cited

U.S. PATENT DOCUMENTS

| | | | | |
|---|---|---|---|---|
| 8,162,950 B2* | 4/2012 | Digeser | ............. | A61B 17/1728 |
| | | | | 606/96 |
| 10,653,432 B2* | 5/2020 | Luttrell | ................. | A61B 90/11 |
| 10,743,892 B2* | 8/2020 | Krause | ............... | A61B 17/1633 |
| 11,096,758 B2* | 8/2021 | Morey | ............... | A61B 17/3403 |
| 11,464,526 B2* | 10/2022 | Aebi | ................. | A61B 17/1622 |
| 2003/0040753 A1* | 2/2003 | Daum | ................ | A61B 17/3462 |
| | | | | 606/96 |
| 2008/0015639 A1* | 1/2008 | Bjork | .................... | A61B 90/11 |
| | | | | 606/240 |
| 2015/0119943 A1* | 4/2015 | Milella, Jr. | ........ | A61B 17/1728 |
| | | | | 606/280 |
| 2018/0338812 A1* | 11/2018 | Morey | .................. | A61B 90/11 |

* cited by examiner

DRILL GUIDE ASSEMBLY

CROSS-REFERENCE TO RELATED APPLICATIONS

This application is a divisional of U.S. patent application Ser. No. 16/260,689 filed on Jan. 29, 2019 entitled "Drill Guide Assembly," which claims priority to U.S. Provisional Patent Application Ser. No. 62/728,946, filed on Sep. 10, 2018 and entitled "Drill Guide Assembly," and U.S. Provisional Patent Application Ser. No. 62/623,643, filed on Jan. 30, 2018 and entitled "Two-Piece Drill Guide Sleeve with Pivoting Head for Drill Guide Assembly," the entireties of which are incorporated herein by reference.

BACKGROUND OF THE INVENTION

1. Field of the Invention

The present invention is directed generally to surgical tools and instruments and, more particularly, to a drill guide assembly for accurate and stable drilling of a bone tunnel.

2. Description of Related Art

During orthopedic surgeries, holes are often drilled in bones. In some procedures, a drill guide, such as that shown in FIG. 1, is used to line-up the drill to ensure the drilled tunnel is in the appropriate location. Many bone surfaces to be drilled have severe contours that vary from patient to patient. Due to the contours, it can be difficult to properly seat the drill guide against the bone. This is particularly true when the drill guide is used to assist in drilling a tibial tunnel during ACL reconstruction.

Many conventional drill guide assemblies are used in conjunction with a guide arm and a drill guide sleeve. Conventional drill guide assemblies also require a threaded mechanism to prevent the guide arm from falling out of the drill guide assembly. Further, many traditional drill guide sleeves have a fixed geometry. These sleeves are malleted into place into the bone, which can cause misalignment.

Therefore, there is a need for a drill guide assembly that can accommodate different anatomies or drill diameters, and a drill guide sleeve for stable placement of the drill guide assembly.

SUMMARY OF THE INVENTION

The present invention is directed to a drill guide assembly that is optimal for accurate and stable drilling of a bone tunnel. According to one aspect, the drill guide assembly includes a guide body having a first end and a second end, and a slot extending from the first end toward the second end. The drill guide assembly also includes a curved guide arm comprising a first arm connected at an angle to a second arm. The first arm terminates in a distal tip. The second arm comprises a first side and a second side, and is slidable within the slot of the guide body. The second arm also includes a plurality of detents along its second side. A locking mechanism is attached at the first end of the guide body. In a first position, the locking mechanism is engaged with one of the plurality of detents.

According to another aspect, the drill guide assembly includes a guide body having a first end and a second end, and a slot extending from the first end toward the second end. The drill guide assembly also comprises a curved guide arm having a first arm connected at an angle to a second arm. The first arm terminates in a distal tip and the second arm is slidable within the slot of the guide body. The drill guide assembly further comprises a clamp mechanism attached at the second end of the guide body. In a first position, the clamp mechanism forms an aperture with the guide body. The aperture has an opening with a width that decreases toward the aperture.

According to another aspect, the present invention is a drill guide sleeve. The drill guide sleeve includes a cannulated sleeve extending distally and connected to a ball. The drill guide sleeve also includes a socket connected to the ball. The socket is movable between a first position and a second position relative to the cannulated sleeve. A pivoting head extends from the socket. In the first position and the second position, the cannulation of the cannulated sleeve is maintained.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
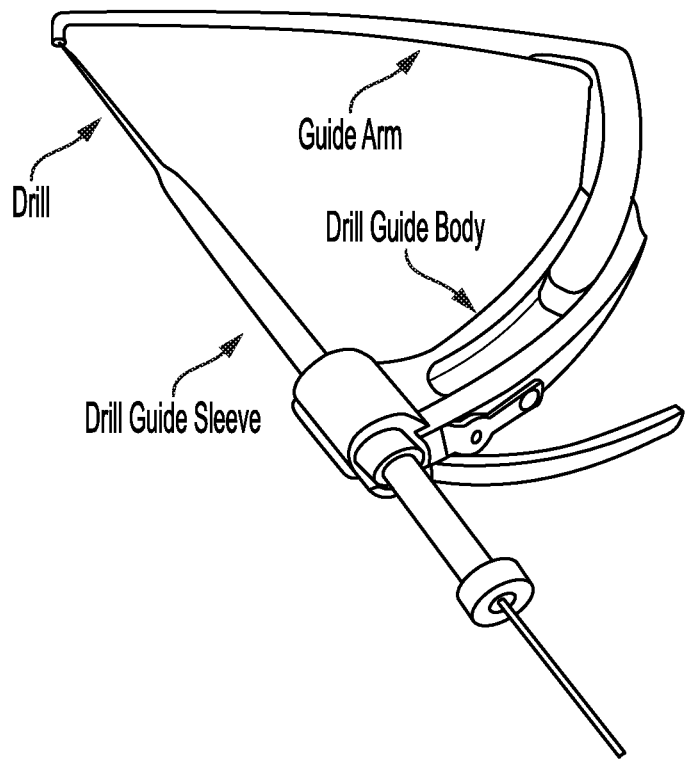
FIG. 1 is a perspective view schematic representation of a drill guide assembly of the prior art.
Figure 2:
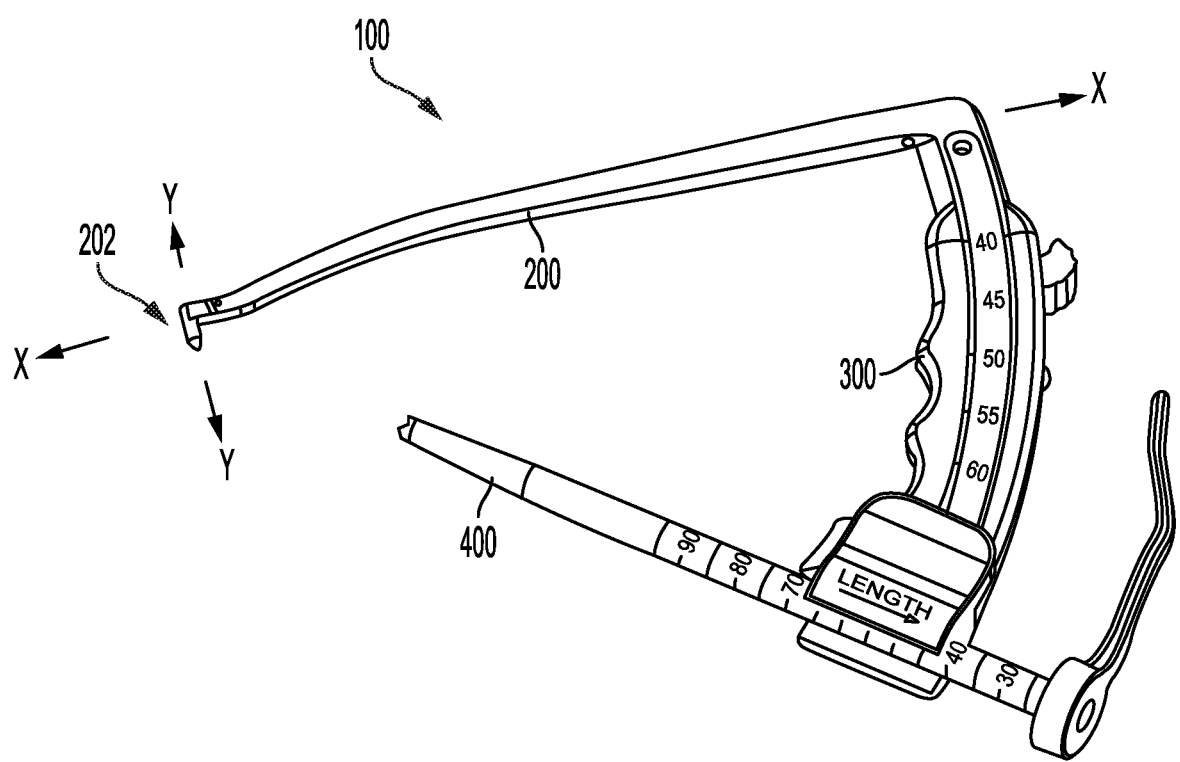
FIG. 2 is a perspective view schematic representation of a drill guide assembly, according to an embodiment.

Referring now to the figures, wherein like reference numerals refer to like parts throughout, FIG. 2 shows a perspective view schematic representation of a drill guide assembly 100, according to an alternative embodiment. The drill guide assembly 100 comprises a curved or bent guide arm 200 connected to and extending from a guide body 300. The drill guide assembly 100 also includes a drill guide sleeve 400 slidable within the guide body 300. In the depicted embodiment, the guide arm 200 extends along a first axis x-x. The guide arm 200 terminates in a distal tip 202. The distal tip 202 extends along a second axis y-y, which is approximately perpendicular to the first axis x-x. As shown in FIG. 2, the distal tip 202 extends in a direction toward the guide sleeve 400.

Figure 3A:
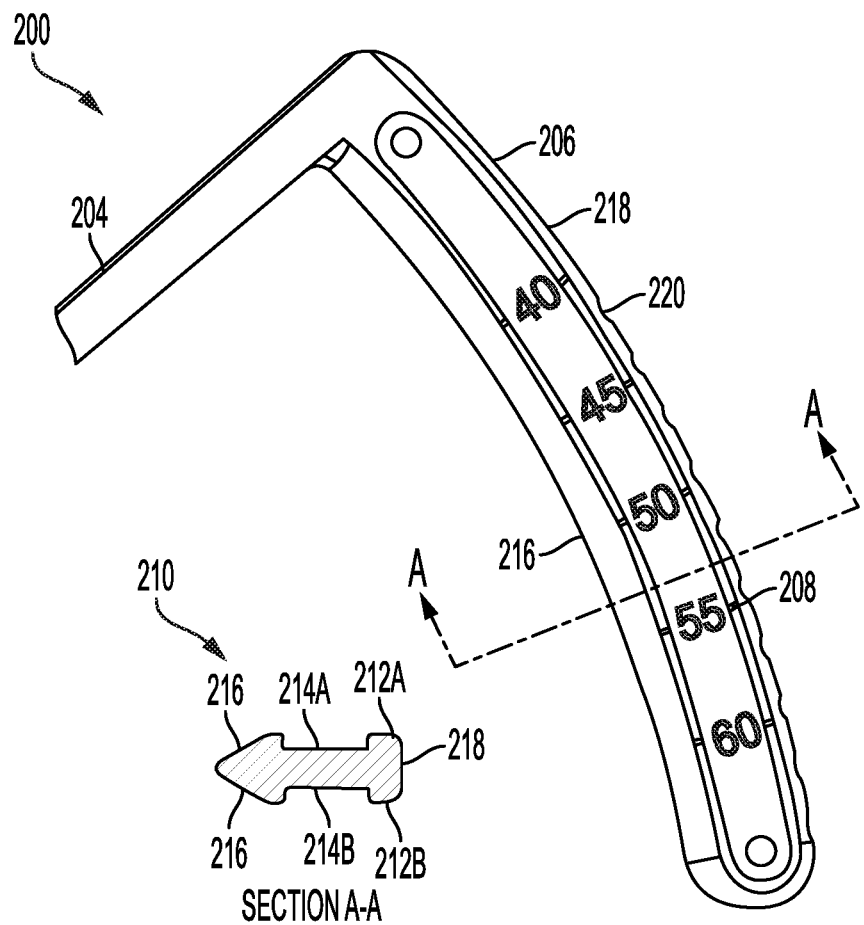
FIG. 3A is a detail view schematic representation of the guide arm, according to an embodiment.
Figure 3B:
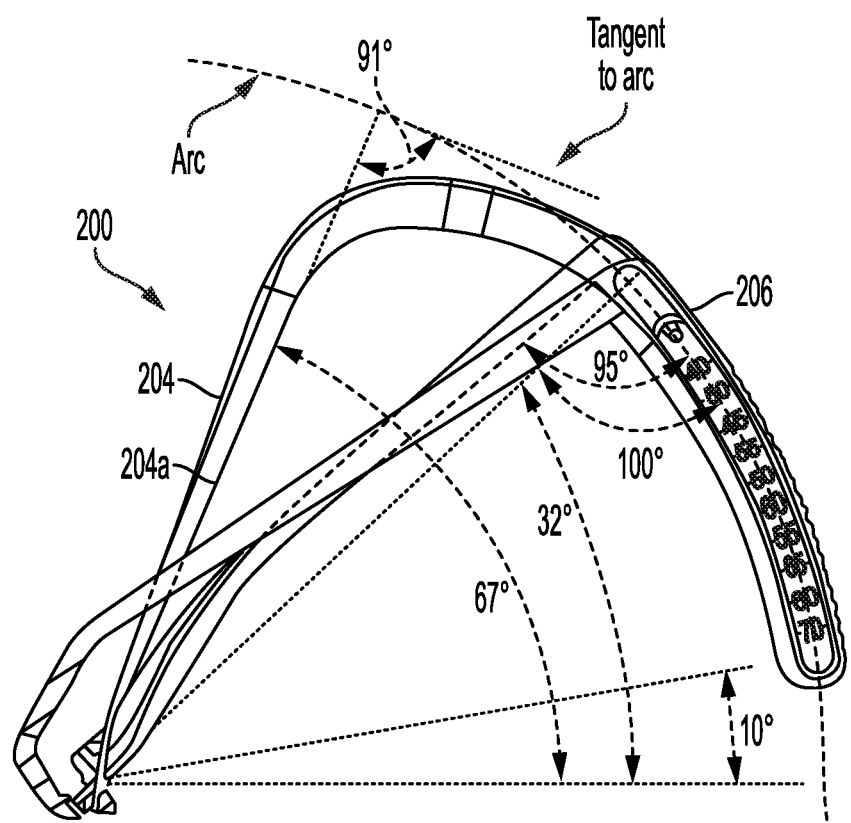
FIG. 3B is another detail view schematic representation of the guide arm with angular measurements, according to an embodiment.

Turning now to FIG. 3A, there is shown a detail view schematic representation of the guide arm 200, according to an embodiment. In the depicted embodiment, the guide arm 200 is comprised of a first arm 204 connected at angle (80°-110°) to a second arm 206. In a preferred embodiment, the first arm 204 is connected to the second arm 206 at angle within the range of 90°-100°. As shown in FIG. 3B, the angle between the first arm 204 and the second arm 206 is measured between a bottom edge 204a of the first arm 204 to the tangent of the arc of the second arm 206. The first arm 204 extends to the distal tip 202 and the second arm 206 is connected to the guide body 300 (FIG. 2).

Still referring to FIG. 3A, the second arm 206 comprises indicators 208. The indicators 208 are printed, etched, or otherwise formed on the second arm 206 and denote the positioning of the guide sleeve 400 relative to the distal tip 202. In FIG. 3A, section A-A shows a cross-section 210 of the second arm 206. As shown in the cross-section 210, the second arm 206 comprises a first surface 212A with a first recess 214A and an opposing second surface 212B with a second recess 214B. In the depicted embodiment, the first recess 214A and the second recess 214B are aligned (alternatively, they are not aligned). In addition, in the depicted embodiment, the first recess 214A and the second recess 214B have rectangular cross-sections. As also shown in FIG. 3A, the second arm 206 is tapered toward a first side 216 (also referred to as an "angled side"). In the depicted embodiment, the second arm 206 is tapered distally, in a direction toward the distal tip 202. The second arm 206 further comprises detents 220 or other similar grooves along a second side 218 (also referred to as a "flat side") opposing the first side 216. The detents 220 facilitate attachment and movement of the guide body 300 along the second arm 206.

Figure 4:
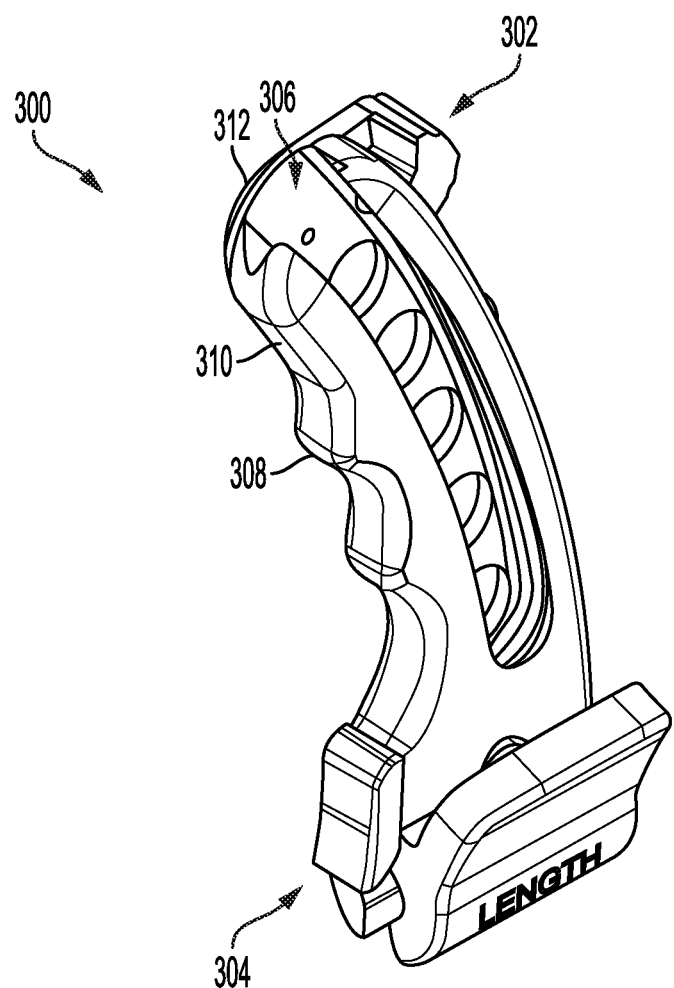
FIG. 4 is a perspective view schematic representation of the guide body, according to an embodiment.

Referring now to FIG. 4, there is shown a perspective view schematic representation of the guide body 300, according to an embodiment. The guide body 300 comprises a locking mechanism 302 and a clamp mechanism 304. The guide body 300 comprises a slot 306 (or track) sized and configured to receive the second arm 206. In the depicted embodiment, the guide body 300 has one or more ridges 308 (or other protrusions) on a first side 310 of the guide body 300 to improve the user's grip on the drill guide assembly 100.

Figure 5:
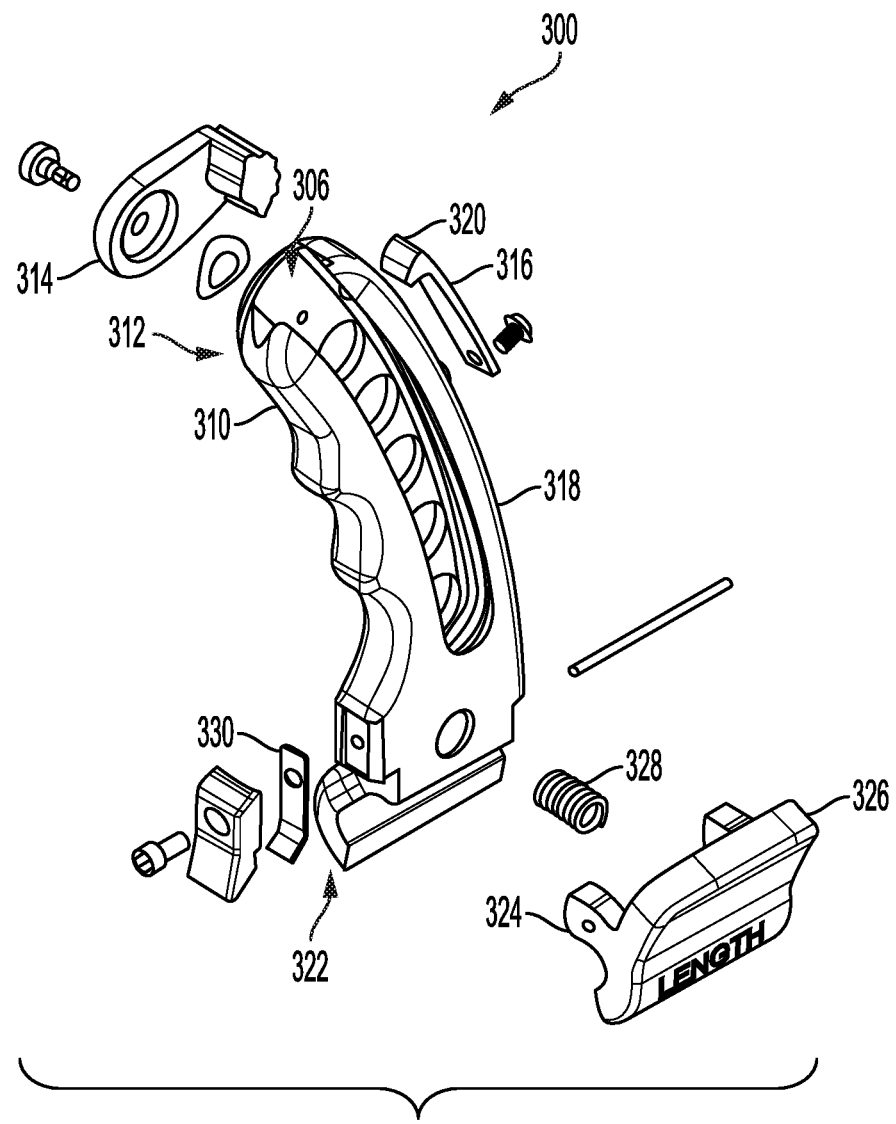
FIG. 5 is an exploded perspective view schematic representation of the guide body, according to an embodiment.

Turning now to FIG. 5, there is shown an exploded perspective view schematic representation of the guide body 300, according to an embodiment. The locking mechanism 302 is attached to the guide body 300 at a first end 312 of the guide body 300. The locking mechanism 302 includes a locking lever 314 rotatably attached to the first end 312 of the guide body 300 such that it can be depressed or rotated toward the guide body 300. The locking lever 314 is attached to the guide body 300 using screws or any other similar known connectors. The locking mechanism 302 additionally comprises a spring 316 (also referred to as a "spring lock") attached to a second side 318 of the guide body 300. The spring lock 316 is attached to the guide body 300 using screws or any other similar known connectors.

Figure 6:
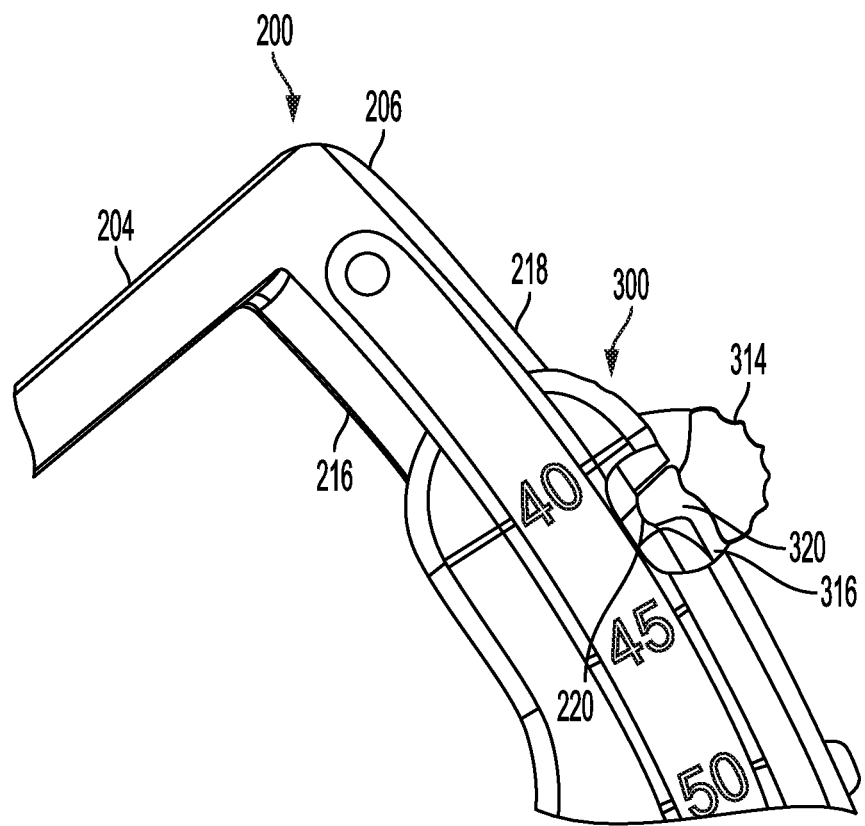
FIG. 6 is a close-up view schematic representation of the guide arm in a locked, second position, according to an embodiment.

Turning now to FIG. 6, there is shown a close-up view schematic representation of the guide arm 200 in a locked, second position, according to an embodiment. As stated above, the second arm 206 of the guide arm 200 comprises detents 220 or detent areas on its second side 218. The detents 220 are configured to interact with the spring lock 316 of the locking mechanism 302, as shown in FIG. 6. As the second arm 206 slides within the slot 306 of the guide body 300, a head 320 of the spring lock 316 catches on or moves into each of the detents 220 to a first position. The interaction of the spring lock 316 and the detents 220 allows for the angle of the curve or bend in the guide arm 200 (i.e., the angle of the first arm 204 relative to the second arm 206) to be adjusted without risking the guide arm 200 falling out of the guide body 300 and out of the sterile field at the surgical site. The spring lock 316 provides enough force to lightly hold the guide arm 200 at the detents 220 in the first position but allows for the guide arm 200 to move within the slot 306 (or track) of the guide body 300 through the range of motion.

When the guide arm 200 is at the desired angle, the spring lock 316 can be locked into the detent 220 (set at preset increments) by engaging the locking lever 314. The locking lever 314 is used to lock the spring lock 316 in place and prevent the guide arm 200 from moving. The locking lever 314 is rotated or depressed from an unlocked, first position, disengaged from the spring lock 316, to a locked, second position, engaging the spring lock 316. When the spring lock 316 is engaged with the locking lever 314 in the second position, it applies a force to the flat side 218 (FIG. 3A) of the second arm 206 that forces the angled side 216 (FIG. 3A), centering it in the guide body 300. Centering the second arm 206 while locking it improves the accuracy of the drill guide assembly 100. The guide body 300 has a corresponding geometry.

Turning back to FIG. 5, the clamp mechanism 304 is attached to the guide body 300 at a second end 322 (opposing the first end 312) of the guide body 300. The clamp mechanism 304 comprises a clamp 324 having a clamp lever 326 extending therefrom, a compression spring 328, and a ratchet spring 330. In the depicted embodiment, the ratchet spring 330 is attached to the first side 310 of the guide body 300 using screws or any other similar known connectors.

Figure 7:
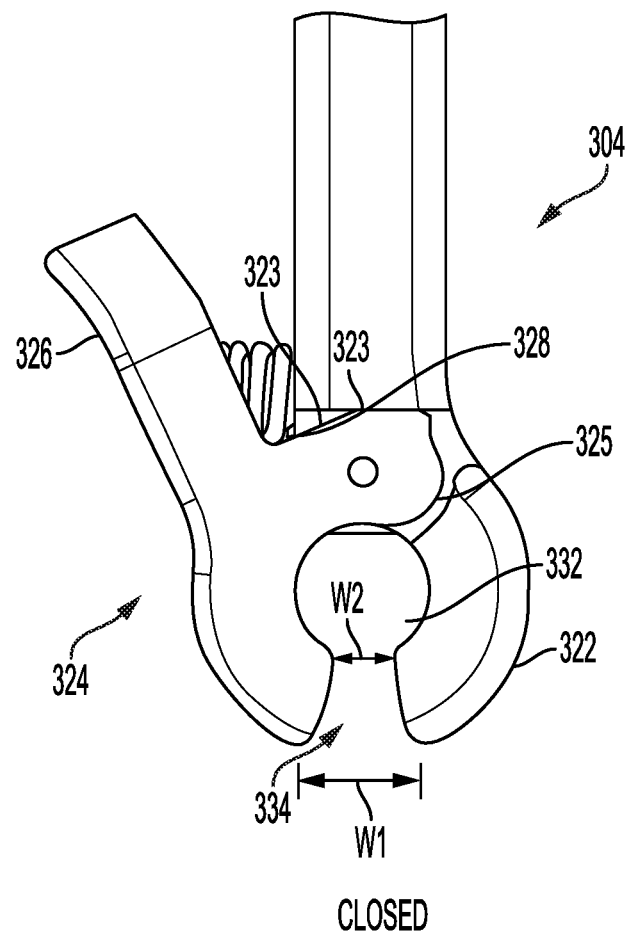
FIG. 7 is a close-up view schematic representation of the clamp in a closed, first position, according to an embodiment.
Figure 8:
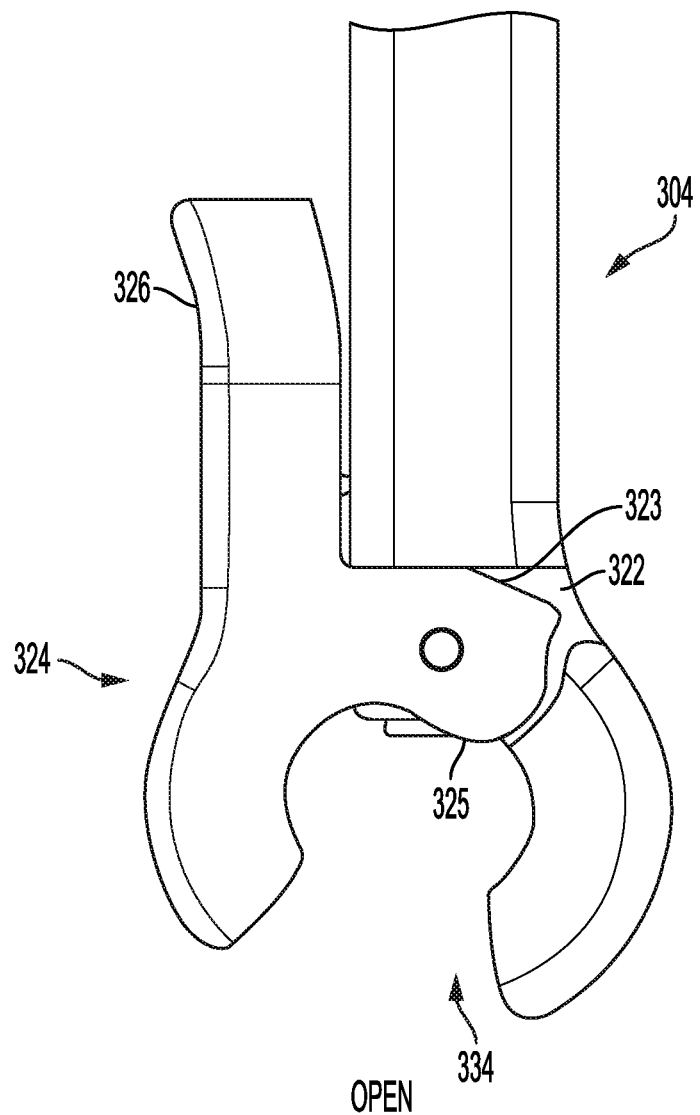
FIG. 8 is a close-up view schematic representation of the clamp in an open, second position, according to an embodiment.

Referring now to FIGS. 7 and 8, there are shown close-up views schematic representations of the clamp 324 in a closed, first position and an open, second position, respectively, according to an embodiment. The clamp 324 is used to hold the guide sleeve 400. Accordingly, the clamp 324 is movable or rotatable between a closed, first position and an open, second position. The clamp 324 maintains the closed, first position shown in FIG. 7 using the compression spring 328. When the clamp 324 is in the closed, first position, the clamp 324 comprises an opening 334 such that the guide sleeve 400 can be easily inserted into the clamp 324. However, the clamp lever 326 must be utilized (i.e., depressed or rotated toward the guide body 300), moving the clamp 324 to the open, second position, to remove the guide sleeve 400 from the clamp 324.

In the closed, first position (FIG. 7), the guide sleeve 400 can fit through the opening 334 because the geometry allows for guide sleeve 400 to act against the wedge geometry of the clamp 324. Because the width (w1 and w2) of the opening 334 decrease toward an aperture 332 created in the clamp 324, once the guide sleeve 400 is inserted, it is difficult to remove the guide sleeve 400 without using the clamp lever 326. The clamp 324 has flats 323 to define the limits for the open, second position (FIG. 8) and the closed, first position (FIG. 7). The clamp 324 also has a feature 325 that helps to eject the guide sleeve 400 when the clamp 324 is moved to the open, second position (FIG. 8). In FIGS. 7-8, the feature 325 is a rounded bump that assists in ejection of the guide sleeve 400.

Figure 9:
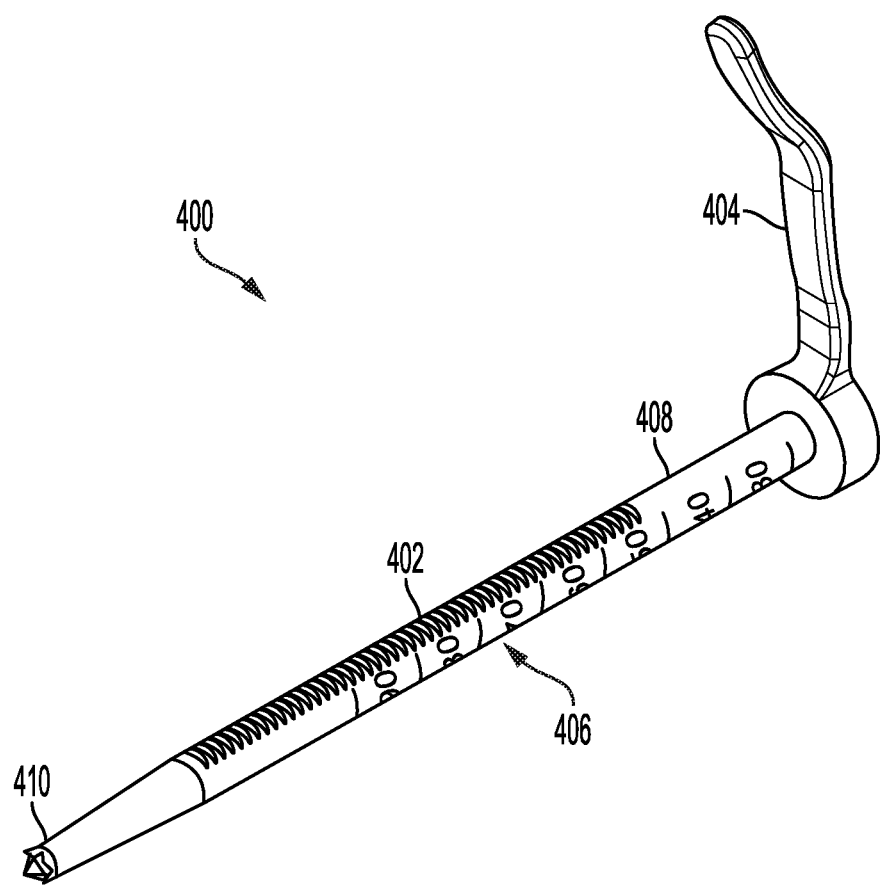
FIG. 9 is a perspective view schematic representation of a guide sleeve, according to an embodiment.

Referring now to FIG. 9, there is shown a perspective view schematic representation of a guide sleeve 400, according to an embodiment. The guide sleeve 400 comprises a cannulated sleeve 408 with a ratchet feature 402 (e.g., ratchet notches) along its length that interacts with the ratchet spring 330 of the clamp mechanism 304. The ratchet spring 330 prevents the retraction of the guide sleeve 400 in the clamp 324 when in a specific rotational orientation. When the guide sleeve 400 is rotated in either direction away from the ratchet spring 330, the guide sleeve 400 can be retracted.

Still referring to FIG. 9, the cannulated sleeve 408 of the guide sleeve 400 extends distally to a jagged distal end 410 for interfacing with bone. The guide sleeve 400 may comprise a strike plate 404 which can be struck by a mallet to insert the guide sleeve 400 into bone. In the depicted embodiment, the guide sleeve 400 comprises a "pusher" 404 (i.e., lever or handle) that can be used to push the guide sleeve 400 into bone, eliminating the use of a mallet. The geometry is such that one hand can grab the guide body 300 and the pusher 404 and squeeze to insert the guide sleeve 400 into bone while simultaneously ratcheting the guide sleeve 400 in the clamp 324. This allows for one-handed operation to rigidly fix the guide body 300 to the anatomy. The pusher 404 also orients with the ratchet notches 402 and allows for easy retraction of the guide sleeve 400. In the depicted embodiment, the guide sleeve 400 also comprises indicators 406 (or other markings) to assist the surgeon with calculating tunnel depth. These indicators 406 may be printed, etched, or otherwise formed on the guide sleeve 400.

Figure 10:
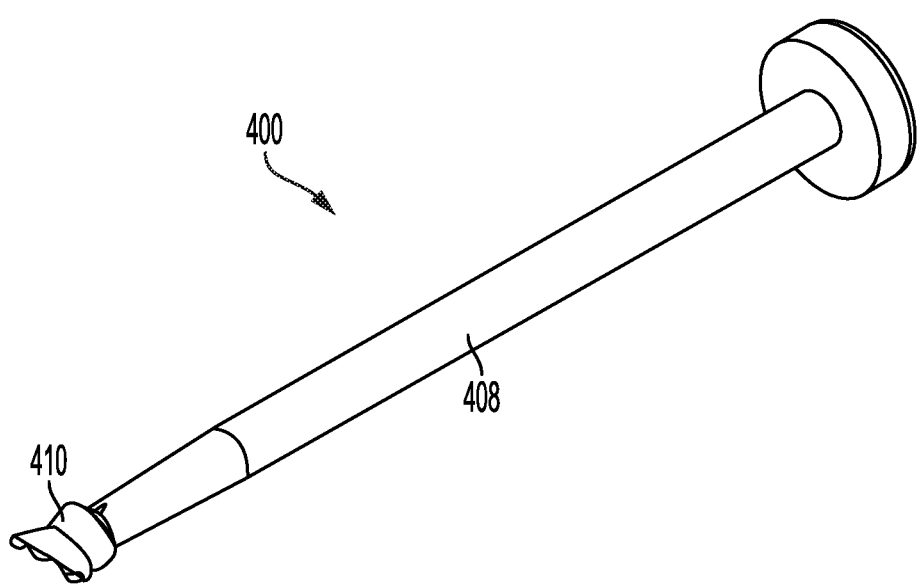
FIG. 10 is a perspective view schematic representation of a guide sleeve, according to an alternative embodiment.
Figure 11:
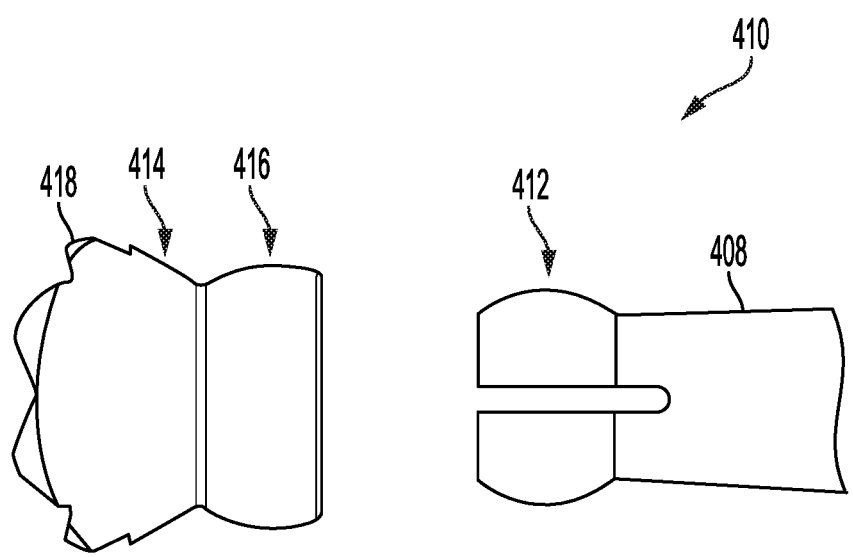
FIG. 11 is a top view schematic representation of the distal pivoting mechanism, according to an embodiment.
Figure 12:
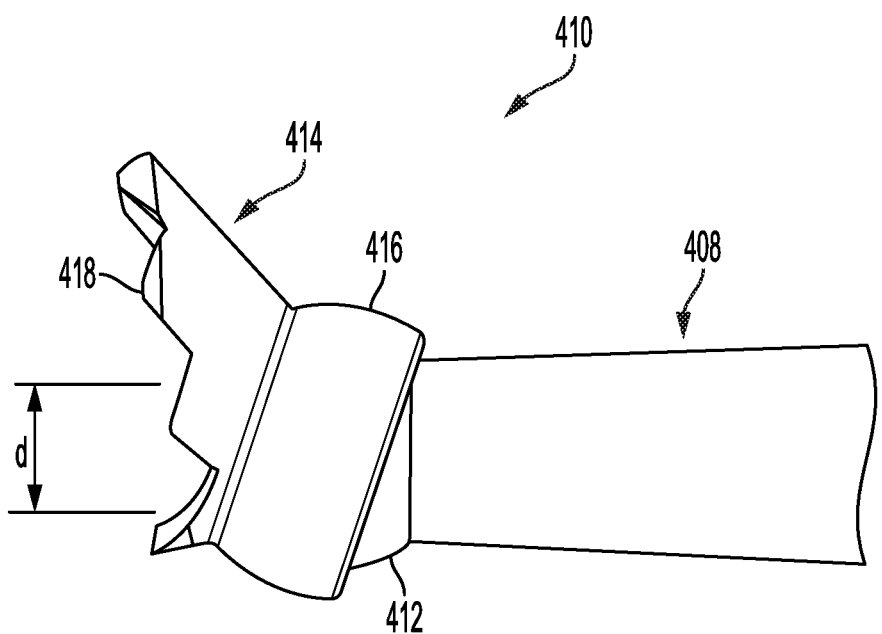
FIG. 12 is a side view schematic representation of the distal pivoting mechanism in a superior, first position, according to an embodiment.
Figure 13:
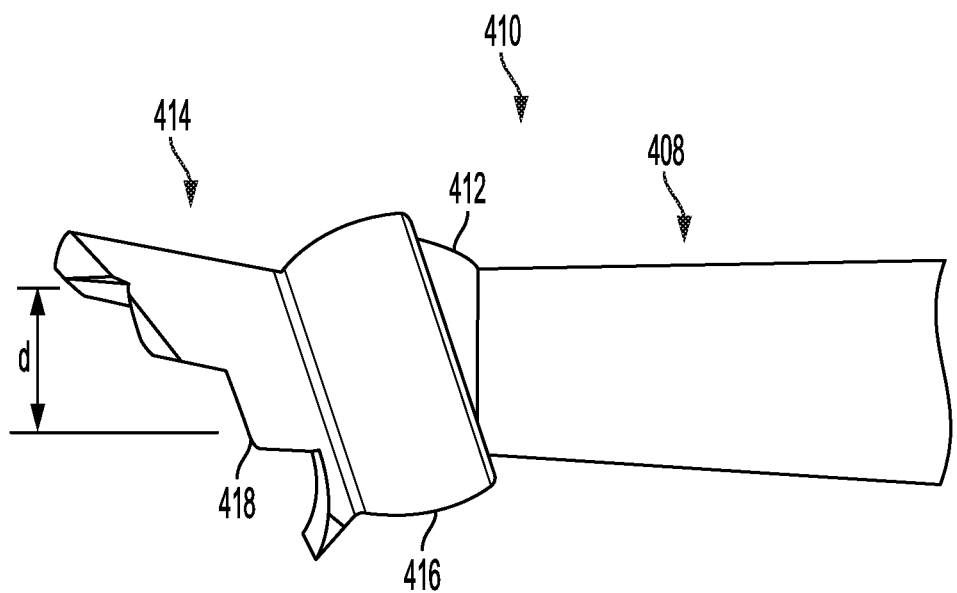
FIG. 13 is a side view schematic representation of the distal pivoting mechanism in an inferior, second position, according to an embodiment.

Turning now to FIG. 10, there is shown a perspective view schematic representation of a guide sleeve 400, according to an alternative embodiment. The guide sleeve 400 in FIG. 10 is a two-piece guide sleeve comprising a cannulated sleeve 408 connected to a jagged distal end 410. In the depicted embodiment, the jagged distal end 410 is a distal pivoting mechanism. As shown in FIG. 11, the distal pivoting mechanism 410 comprises a ball 412 and a pivoting head 414 with a socket 416. The pivoting head 414 extends from the socket 416. In the depicted embodiment, the pivoting head 414 is "crown-shaped" such that it is comprised of a piece of a sheet of material (e.g., a solid piece of bar stock) extending distally from the circumference of the socket. As shown in FIGS. 11-13, the sheet of material is jagged, comprising one or more distal ridges 418. As shown in FIG. 11, the ball 412 is attached at a distal end of the cannulated sleeve 408. The pivoting head 414 and socket 416 are attached to the ball by either a loose fitting or a design with friction to be positionable (i.e., movable). The configuration of the distal pivoting mechanism 410 allows the pivoting head 414 to be secured against the bone while the cannulated sleeve 408 is rotated.

Referring now to FIGS. 12 and 13, there are shown top views schematic representations of the pivoting head 414 in a superior, first position and an inferior, second position, respectively, according to an embodiment. The rotation of the pivoting head 414 allows the drill guide assembly 100 to have a more stable position against the bone. The pivoting head 414 also maintains cannulation throughout the range of motion of the pivoting head 414 on the cannulated sleeve 408. The two-piece guide sleeve 400 allows for the guide sleeve 400 to be repositioned while maintaining access to the entire diameter d of the cannulated sleeve 408. Therefore, the guide sleeve 400 in FIGS. 10-13 improves stability against the bone without blocking any portion of the diameter d of the cannulated sleeve 408.

Figure 14:
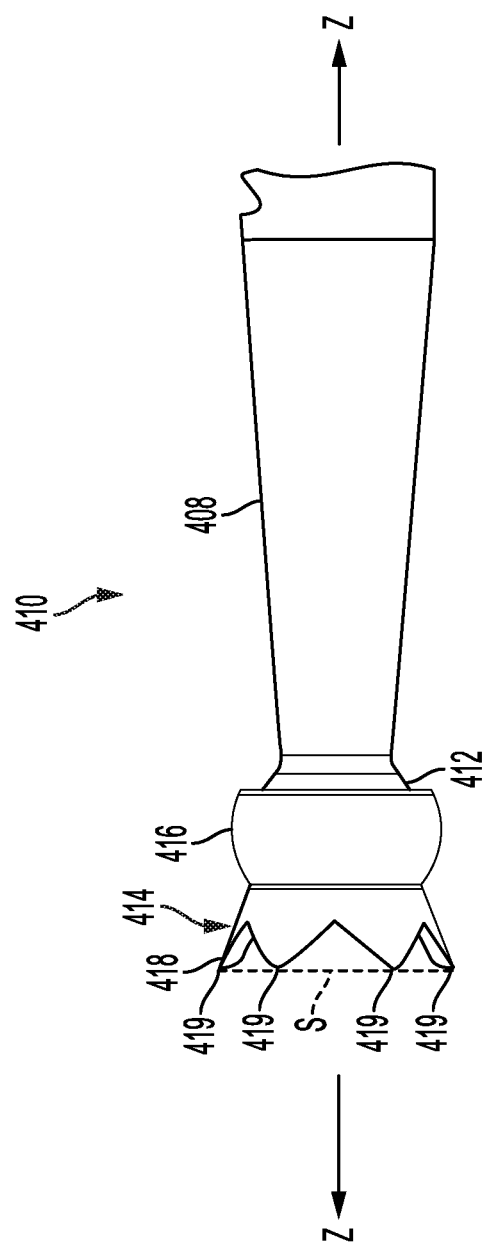
FIG. 14 is a top view schematic representation of the distal pivoting mechanism, according to an alternative embodiment.

Turning briefly to FIG. 14, there is shown a top view schematic representation of the distal pivoting mechanism 410, according to an alternative embodiment. In the depicted embodiment, the cannulated sleeve 408 and distal pivoting mechanism 410 extend along a central longitudinal z-z axis. As shown, each of the distal ridges 418 has a distal tip 419. The pivoting head 414 has a geometry such that the distal tips 419 of the pivoting head 414 are connectable by a straight line s. Stated differently, all the distal tips 419 extend to the same straight line axis s, which extends substantially perpendicular to the central longitudinal axis z-z.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A drill guide sleeve, comprising:
   a cannulated sleeve having an internal diameter, a proximal end and a distal end, wherein the cannulated sleeve extends along a central longitudinal axis, and has a ball connected to the distal end;
   a pivoting head having a proximal portion defining a proximal end and a distal portion defining a distal end, the proximal portion defining a socket and the distal portion including ridges that extend distally with respect to a longitudinal axis of the pivoting head, each of the ridges terminating in a pointed tip which defines the distal end of the pivoting head;
   wherein the socket is connected to the ball and movable between a first position and a second position relative to the cannulated sleeve;
   and
   wherein in the first position and the second position, no portion of the internal diameter of the cannulated sleeve is blocked by the socket or the pivoting head.

2. The drill guide sleeve of claim 1, wherein the pivoting head is comprised of a sheet of material extending distally from a circumference of the socket.

* * * * *